United States Patent
Moyers et al.

(10) Patent No.: US 6,664,543 B2
(45) Date of Patent: Dec. 16, 2003

(54) CONTINUOUS SAMPLING AND DIGITAL INTEGRATION FOR PET SCINTILLATION

(75) Inventors: J. Clifton Moyers, Oak Ridge, TN (US); John W. Young, Knoxville, TN (US); Mark Musrock, Oak Ridge, TN (US)

(73) Assignee: CTI PET Systems, Inc., Knoxville, TN (US)

( * ) Notice: Subject to any disclaimer, the term of this patent is extended or adjusted under 35 U.S.C. 154(b) by 0 days.

(21) Appl. No.: 10/058,568

(22) Filed: Jan. 28, 2002

(65) Prior Publication Data

US 2003/0213913 A1 Nov. 20, 2003

(51) Int. Cl.[7] .................................................. G01T 1/20
(52) U.S. Cl. .................................. 250/369; 250/363.03
(58) Field of Search ........................... 250/369, 363.03, 250/363.04

(56) References Cited

U.S. PATENT DOCUMENTS

| | | | |
|---|---|---|---|
| 4,881,171 A | * 11/1989 | Jatteau et al. | 250/363.02 |
| 5,440,124 A | * 8/1995 | Kelly et al. | 250/309 |
| 5,585,637 A | 12/1996 | Bertelsen et al. | |
| 5,841,140 A | 11/1998 | Mc Croskey et al. | |
| 6,232,604 B1 | * 5/2001 | McDaniel et al. | 250/363 |
| 6,252,232 B1 | * 6/2001 | McDaniel et al. | 250/369 |
| 6,297,506 B1 | * 10/2001 | Young et al. | 250/369 |
| 6,392,236 B1 | * 5/2002 | Mackawa et al. | 250/369 |

OTHER PUBLICATIONS

P. Bailly, et al., "The DIRC Front–end Electronics Chain for BaBar," Transactions on Nuclear Science, Dec. 2000, vol. 47 No. 6, pp. 2106–2113.

Hilsenrath, et al., "A Single Chip Pulse Processor for Nuclear Spectroscopy," Transactions on Nuclear Science, Feb. 1985, vol. NS–32, pp. 145–149.

Jordanov, et al., "Digital Pulse Processor Using A Moving Average Technique," Conference Record of the Nuclear Science Symposium and Medical Imaging Confence, 1992, vol. 1, pp. 447–449.

C.L. Morris, et al., "A Digital Technique for Neutron–gamma Pulse Shape Discriminator," Nuclear Inst. and Methods, 137 (1976) pp. 397–398.

Takahashi, et al., "A New Pulse Height Analysis System Based on Fast ADC Digitizing Technique," Conference Record of the Nuclear Science Symposium & Medical Imaging Conference, 1992, vol. 1, pp. 350–352.

Jordanov, et al., "Digital Pulse–shape Analyzer Based on Fast Sampling of an Integrated Charge Pulse," Transaction on Nuclear Science, Aug. 1995, vol. 42 No. 4, pp. 683–687.

A. Geraci, et al., "Shaping the Quantization Noise in High Resolution Digital Spectroscopy: Theory and Experiments," Conference Record of the Nuclear Science Symposium & Medical Imaging Conference, 1997, vol. 1, pp. 18–21.

P. Fuchs, "The Development of an Object–Oriented System Which Integrates Simulation and Reconstruction Within a Common Framework," Paper presented at AIHEP Workshop on New Computing Techniques in Physics Research in Pisa, Apr. 1995.

* cited by examiner

*Primary Examiner*—Christopher W. Fulton
*Assistant Examiner*—Tania C. Courson
(74) *Attorney, Agent, or Firm*—Pitts & Brittian, P.C.

(57) ABSTRACT

An apparatus and method for determining the total energy of a continuously under-sampled energy signal resulting from an annihilation event detected by a positron emission tomograph (PET) scanner. An annihilation event is detected by a scintillator crystal and photomultiplier tube, which produces an energy signal that is continuously under-sampled by an analog-to-digital converter. The start time of the energy signal is determined by a constant fraction discriminator and time-to-digital converter. The start time is used to calculate a new amplitude for each sample, from which the total energy can be calculated.

14 Claims, 4 Drawing Sheets

CONTINUOUS SAMPLING AND DIGITAL INTEGRATION FOR PET SCINTILLATION

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of Invention

This invention relates to the field of gamma ray detection in a positron emission tomograph (PET) imaging system. More specifically, the invention involves apparatus and methods for determining the total energy of a continuously under-sampled energy signal utilizing the measured event arrival time.

2. Description of the Related Art

In a positron emission tomograph (PET) imaging system, a patient is injected with a radioactively tagged substance that the body normally metabolizes in some fashion. The radioactive tag used is a positron-emitting isotope of either an element found in the substance or an element that is substituted for another element in the substance. For example, a widely used isotope is the positron-emitting isotope of fluorine, $^{18}F$. This isotope is substituted, through a chemical synthesis process, for hydrogen in complex compounds such as glucose-forming fluro-deoxyglucose (FDG). When FDG is injected into a patient, the body will attempt to use it in the same fashion as it would normal glucose. Thus, there will be higher concentrations of positron emitters in areas where glucose is metabolized at higher levels, such as the brain, muscle tissue (the heart), and tumors.

As the FDG or other radiopharmaceutical isotopes decay in the body, they discharge positively charged particles called positrons. Upon discharge, the positrons encounter electrons, and both are annihilated. As a result of each annihilation event, gamma rays are generated in the form of a pair of diametrically opposed photons approximately 180 degrees (angular) apart. By detecting these annihilation "event pairs" for a period of time, the isotope distribution in a cross section of the body can be reconstructed. These events are mapped within the patient's body, thus allowing for the quantitative measurement of metabolic, biochemical, and functional activity in living tissue. More specifically, PET images (often in conjunction with an assumed physiologic model) are used to evaluate a variety of physiologic parameters such as glucose metabolic rate, cerebral blood flow, tissue viability, oxygen metabolism, and in vivo brain neuron activity.

Mechanically, a PET scanner consists of a bed or gurney and a gantry, which is typically mounted inside an enclosure with a tunnel through the center, through which the bed traverses. The patient, who has been treated with a radiopharmaceutical, lies on the bed, which is then inserted into the tunnel formed by the gantry. Traditionally, PET scanners are comprised of one or more fixed rings of detectors, surrounding the patient on all sides. Some newer scanners use a partial ring of detectors and the ring revolves around the tunnel. The gantry contains the detectors and a portion of the processing equipment. Signals from the gantry are ultimately fed into a computer system where the data is then processed to produce images. Detectors on the detector rings encircling the patient detect the gamma rays, one on either side of the patient. The processing electronics determine when in time each gamma ray occurs. Therefore, when two detectors on opposite sides of the patient have detected gamma rays that occurred within some time window of each other, it is safe to assume that the positron-electron interaction occurred somewhere along the line connecting the two detectors.

The scanner detectors use a scintillator to detect the gamma rays. Suitable material used for the scintillator includes, but is not limited to, either lutetium oxyorthosilicate (LSO) or bismuth germanate (BGO). The output from the scintillator is in the form of light pulses corresponding to the interactions of gamma rays within the crystal. A photodetector, typically a photomultiplier tube (PMT) or an avalanche photodiode, detects the light pulses and converts them into electrical signals, which are filtered and sent to a processing system.

To accurately measure the energy absorbed from a gamma ray interacting in the detector, the total light from a crystal scintillation event must be determined by integrating the signal (light detected by the PMT). This integration is traditionally performed using analog circuitry via a gated integrator or using the summation of digital samples of the signal. However, in order to get a good estimate of the energy using digital integration, one must acquire a sufficient number of samples of the energy signal. The energy estimate degrades as the number of samples decreases. The practical sampling rate is limited by commercially available analog-to-digital converters (ADC). This sampling limit is typically not a problem for energy signals of long duration. However, for short duration scintillation signals, the sampling frequency may limit the number of samples to as few as four or five samples.

BRIEF SUMMARY OF THE INVENTION

An apparatus and method for determining the total energy of a continuously under-sampled energy signal resulting from an annihilation event is provided. A gamma ray from an annihilation event interacts with a scintillator crystal, such as lutetium oxyorthosilicate (LSO), which produces a light output sensed by a photomultiplier tube (PMT). The PMT output signal is sensed by a constant fraction discriminator (CFD) followed by a time-to-digital converter (TDC), precisely registering the time of occurrence of the light pulse. The PMT output signal is shaped with a low-pass filter having an approximate 25 ns shaping time used as an anti-aliasing filter, followed by an analog-to-digital converter (ADC). The sample time for the ADC is such that only 3 or 4 samples of the shaped signal are made. The time relationship of the ADC samples to the start of the signal is known due to the known synchronous relationship between the TDC clock and the ADC sample clock. Because the shape of the sampled filtered energy signal is known and by matching the samples to the shape using the TDC time information, a corrected estimate of the actual gamma ray energy can be calculated. The corrected energy of the shaped signal is calculated from the time relationship by calculating a new amplitude for each sample.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

An apparatus and method for determining the total energy of a continuously under-sampled energy signal resulting from an annihilation event is disclosed. A gamma ray from an annihilation event interacts with a scintillator crystal such as lutetium oxyorthosilicate (LSO), which produces a light output sensed by a photomultiplier tube (PMT). The energy signal output from the PMT is illustrated in FIG. 1 as a raw energy signal 102.

Figure 1:
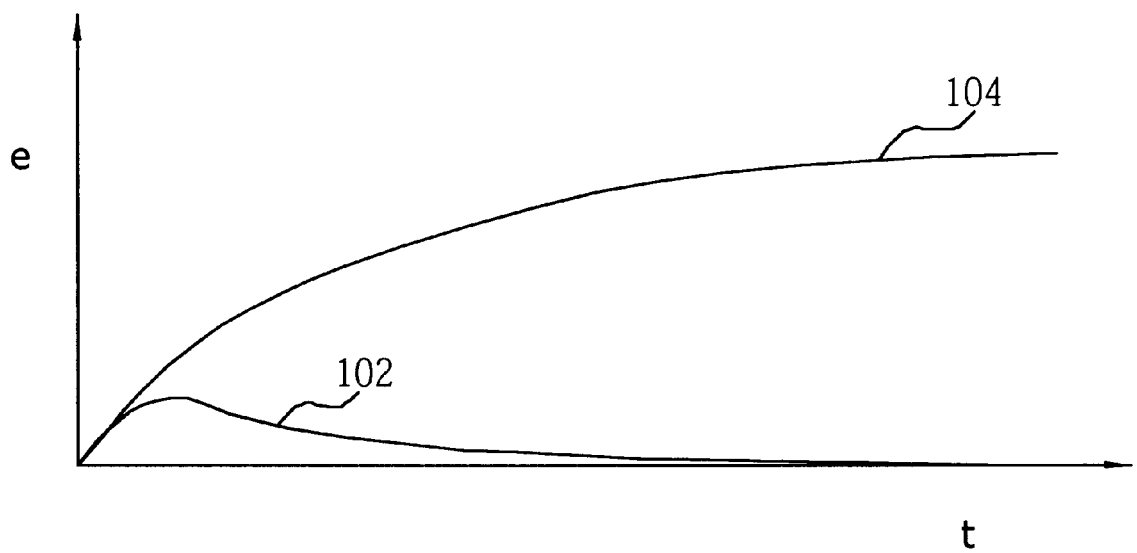
FIG. 1 is a graph showing the relationship of energy to time for both a raw signal and an integrated signal.

FIG. 1 is a graph, over time t, of the energy e detected by the PMT. A raw energy signal 102 is shown, along with an integrated energy signal 104, which is the raw energy signal 102 integrated over time t. The integrated energy signal 104 indicates the total energy in the signal, which is proportional to the energy detected. The energy absorbed from a gamma ray interacting in the crystal is determined by integrating the light from the crystal. The integration is typically performed by a gated integrator or by summing digital samples of the raw energy signal 102.

Figure 2:
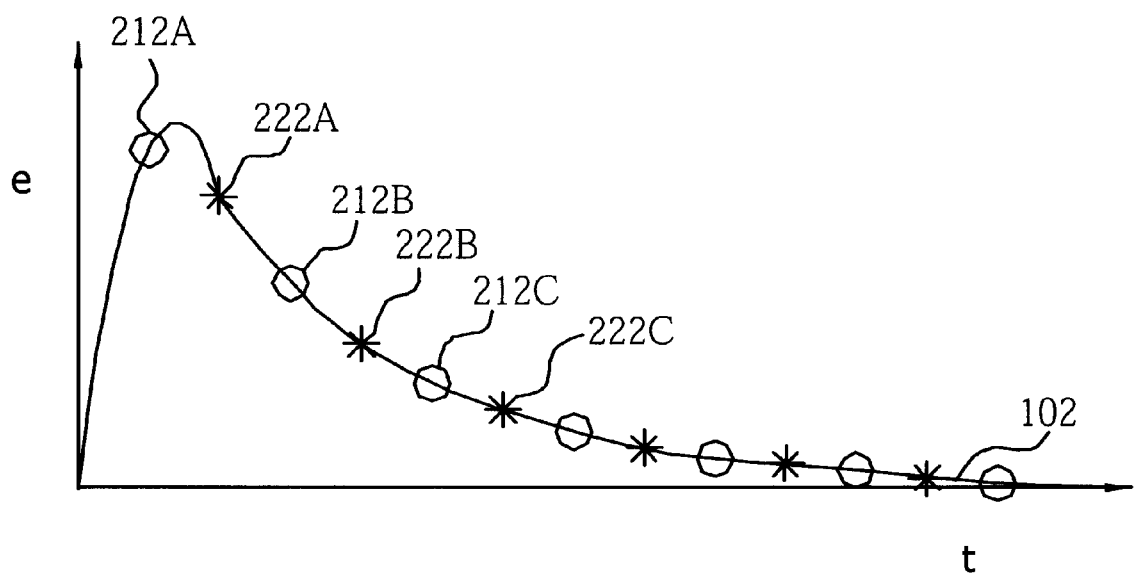
FIG. 2 is a graph showing the relationship of energy to time for an energy signal, including two sampling phases.

FIG. 2 is a graph of the raw energy signal 102 with two sets of sampling points 212, 222. For highly under-sampled raw energy signals, as illustrated in FIG. 2, the estimate of the total energy e in the signal (energy resolution) is degraded due the sampling time t relation to the signal. For example, the energy estimate from the sampling 222 shown in FIG. 2 is different than the energy estimate from the sampling 212.

Figure 3:
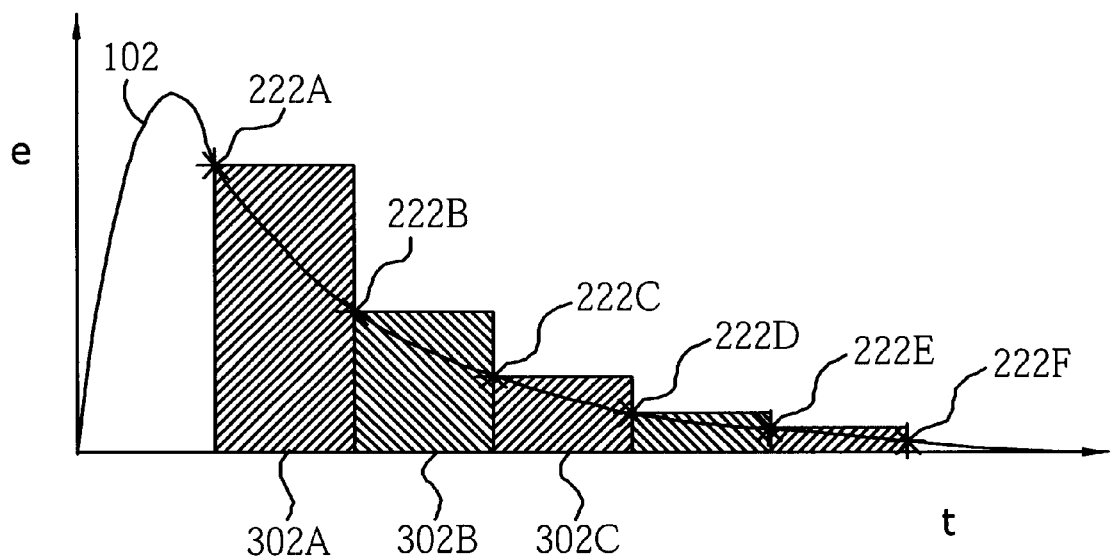
FIG. 3 is a graph of the energy signal sampling points starting at a first point along the time axis.
Figure 4:
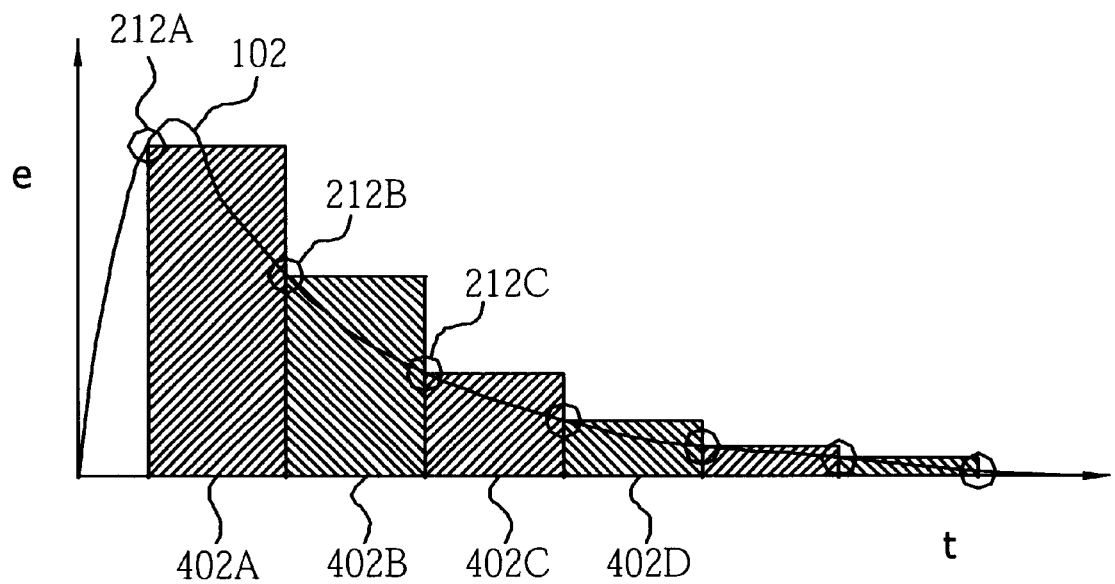
FIG. 4 is a graph of the energy signal sampling points starting at a second point along the time axis.

FIGS. 3 and 4 graphically illustrate the technique of digital integration. Each bar 302, 402 in the graph begins at the time of the sample 212, 222 and ends at the time of the next sample 212, 222, and each bar 302, 402 has an amplitude equal to the amplitude of each sample point 212, 222. The areas of each bar 302, 402 are summed and the summed areas represent the total energy that is calculated from the sampled data. An analog to digital converter (ADC) typically contains a holding circuit that maintains the last sampled value until the next sample point is taken.

The first sample point 212A occurs before the first sample point 222A, and, consequently, the bar graphs 302, 402 illustrated in FIGS. 3 and 4 result in different calculated total energy. If the arrival time of the signal 102 were known, that is, if the time of the first sample point 212A, 222A with respect to the origin of the energy signal 102 illustrated on the figures were known, the sampling points 212, 222 could be shifted along the time axis and the magnitude of each sampling point 212, 222 could be calculated. The correct total energy of the signal can be calculated from the new magnitude values. Conversely, the unscaled samples can be summed and the final integrated result may be rescaled using the time-to-digital converter (TDC) information for magnitude correction.

Figure 5:
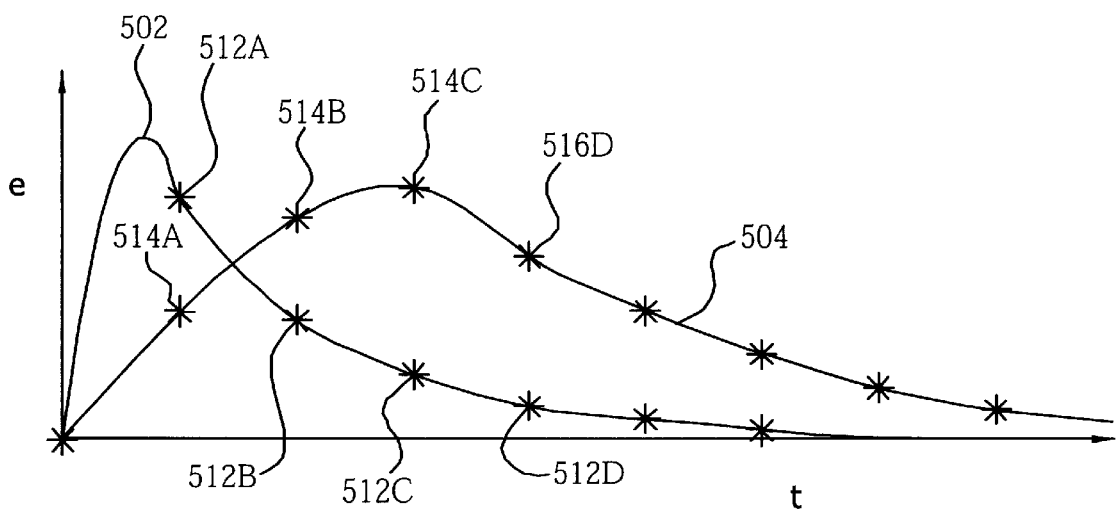
FIG. 5 is a graph of the energy signal and a shaped energy signal.
Figure 8:
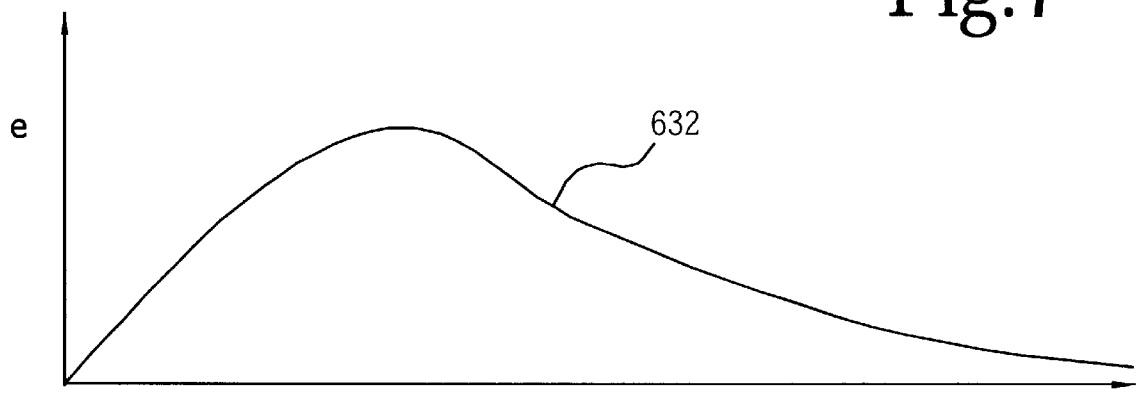
FIG. 8 is a graph of the shaped energy signal.
Figure 9:
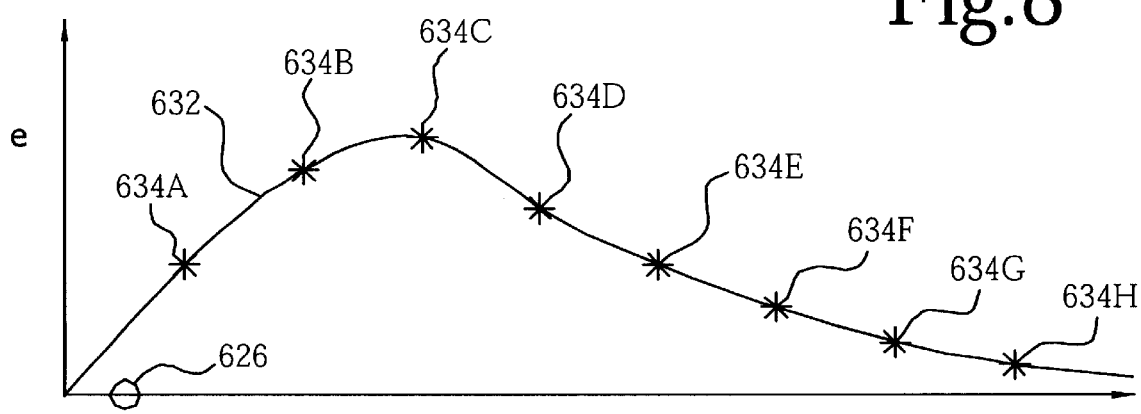
FIG. 9 is a graph of the TDC and ADC signals.

FIG. 5 illustrates the raw energy signal 502 and a shaped energy signal 504. The energy signal 102 of FIGS. 1 through 4 is the energy signal of the raw signal detected by the PMT 604 (illustrated in FIG. 6) and is equivalent to the raw energy signal 502 illustrated in FIG. 5. A shaping filter 612 (illustrated in FIG. 6), as is typically done in nuclear spectroscopy systems, is applied to the energy signal 502 to lengthen the signal over time, allowing more samples to be acquired for a given sampling frequency. The resulting shaped energy signal 504 is shown in FIGS. 5, 8 and 9. Lengthening the raw energy signal 502 has the undesirable effect of increasing the probability of a second event, producing a second energy signal, occurring during the processing of the first signal. If a second event is detected before the processing interval of the first event, the energy of the second event causes the estimate of the first event to be incorrect. Accordingly, to minimize this probability, it is desirable to keep the shaping filter time constant of the energy event to a minimum.

Figure 6:
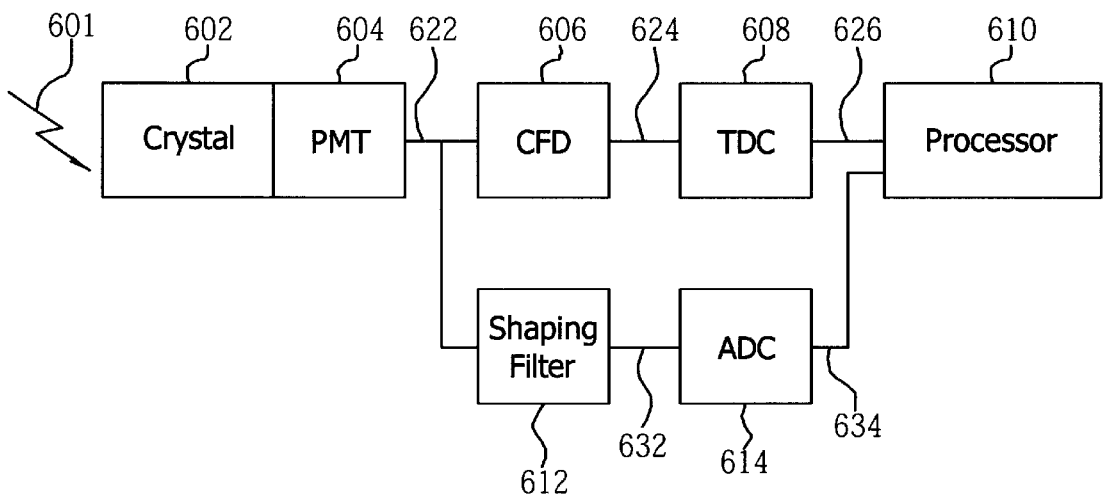
FIG. 6 is a block diagram of the apparatus.

FIG. 6 is a block diagram of a sampling circuit. An event 601 interacts with a scintillator crystal 602 and is detected by a PMT 604. The PMT output 622 feeds a constant fraction discriminator (CFD) 606 that feeds a time-to-digital converter (TDC) 608. The TDC 608 is used to determine the start time of the event 601, within the resolution of the TDC 608 and based on the output of the CFD 606. The PMT output 622 also feeds a shaping filter 612, which has an output 632 feeding a continuously sampling analog-to-digital converter (ADC) 614. The ADC 614 samples the shaped signal 632 from the shaping filter 612, producing a series of sample data representing the amplitude of the shaped signal 632 at the time of sampling. The TDC output 626 and the ADC output 634 are used by a processor 610 to determine total energy of the detected event 601.

The shaping filter 612, in one embodiment, is a low-pass filter having an approximate 25 ns shaping time and is used as an anti-aliasing filter. In one embodiment, the sampling frequency of the ADC 614 is such that as few as 3 samples of the shaped signal 632 are taken. In another embodiment, one sample of the shaped signal 632 is taken. However, the estimate of the total energy is less accurate than with more samples. The time relationship of the ADC 614 samples to the start of the shaped signal 632 is known due to the known synchronous relationship between the TDC 608 clock and the ADC 614 sample clock. Furthermore, the shape of the filtered energy signal 632 is known. Thus, by matching the ADC 614 samples to the shape using the TDC 608 time information, a corrected estimate of the actual gamma ray energy may be calculated. The corrected energy of the shaped signal is calculated from the time relationship by time-shifting the ADC 614 sampled data and calculating a new amplitude for each sample.

The energy estimate degrades as the number of ADC 614 samples decreases. The practical sampling rate is limited by commercially available analog-to-digital converters. This sampling limit is typically not a problem for energy signals of long duration. However, for short duration scintillation signals, the sampling frequency may limit the number of samples of the energy, waveform to as few as four or five samples In one embodiment, the ADC 614 samples every 32 ns, and the TDC 608 resolves time differences in 2 ns steps. However, the calculated phase relationship time difference is resolved only to the nearest 8 ns, which is one-quarter of the sample time. In this embodiment, even with the phase relationship resolved to only one-quarter of the sample time, the sampled energy spectrum is corrected to approximately 1% of the actual full width half maximum (FWHM).

Those skilled in the art will recognize that the shaping time constant, the ADC sampling time, and the TDC resolution can vary without departing from the scope and spirit of the invention. The scintillator crystal 602 can by LSO, LYSO, LGSO, GSO, BGO, or other crystal responsive to the radiation to be measured. Different types of crystals 602 necessitates differing shaping time constants, ADC sampling times, and TDC resolutions.

Figure 7:
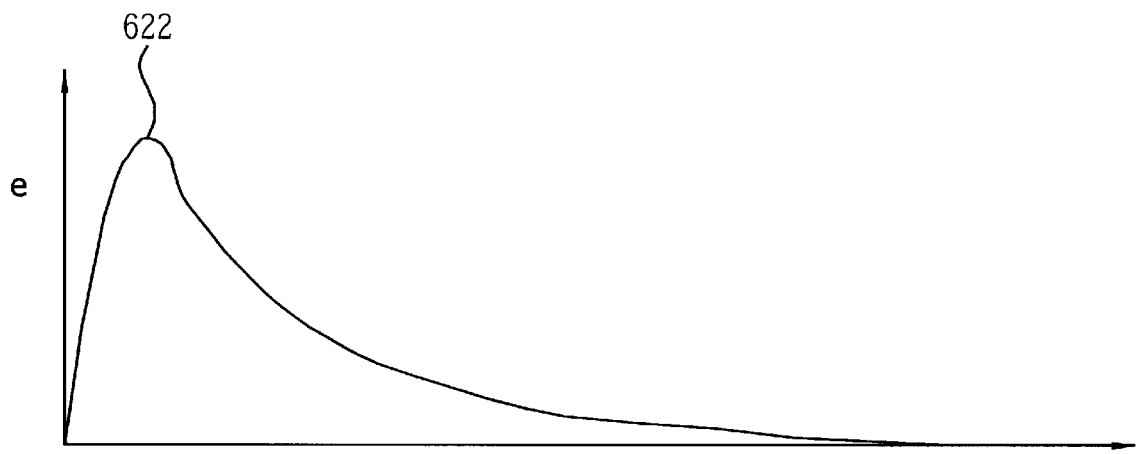
FIG. 7 is a graph of the raw energy signal.

FIG. 7 illustrates the raw energy signal 622 output from the PMT 604 for an event 601 interacting with the scintillator crystal 602. FIG. 8 illustrates the shaped energy signal 632 output from the shaping filter 612. In one embodiment, the crystal 602 is formed of LSO and the shaping filter 612 is a low-pass filter having an approximate 25 ns shaping time.

FIG. 9 illustrates an example of a time 626 at which the TDC 608 precisely registers the time of occurrence of the event 601. The CFD 606 generates a trigger signal 624 when the raw energy signal 622 magnitude exceeds a predetermined level correlated to the spectral energy of the radiation. The TDC 608 generates a timing signal 626 after receiving the trigger signal 624. FIG. 9 also illustrates an example of a series of ADC 614 sample points 634A through 634H. The first ADC 614 sample point 634A can occur at any time between the start of the shaped energy signal 622 and a time equal to the time difference between the ADC 614 samples. The remaining sample points 634B through 634H occur periodically after the first 634A.

The processor 610, illustrated in FIG. 6, uses the information on the time of the start of the raw energy signal 622 to correlate the ADC 614 sample points 634A through 634H to their position on the shaped energy signal 622 curve. After the sample points 634A through 634H position on the shaped energy signal 632 curve are determined, a corrected estimate of the actual gamma ray energy, or the total energy, of the event 601, as represented by the shaped energy signal 632, is calculated. The shape of the shaped energy signal 632 is known and the sampled data points 634A through 634H are matched to the shaped energy signal 632 using the TDC 608 time information. In one embodiment, the corrected energy of the shaped energy signal 632 is calculated by time shifting the sampled data points 634A through 634H by the TDC 608 time and calculating a new amplitude for each sample point 634A through 634H.

From the foregoing description, it will be recognized by those skilled in the art that an apparatus and method for determining the total energy of a continuously undersampled energy signal resulting from an annihilation event has been provided. The shaped output of a PMT is continuously sampled by an ADC. A constant fraction discriminator monitors the PMT output and, in conjunction with a TDC, generates a timing signal related to the start of the event. The total energy of the event is calculated by adjusting the values of the sampled data from the ADC based on the determined time of the event.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

We claim:

1. An apparatus for determining a total energy level for an event detected in a tomograph scanner, said apparatus comprising:

a detector responsive to the event and producing an energy signal;

a shaping circuit responsive to said energy signal and producing a shaped signal;

an analog-to-digital converter continuously sampling said shaped signal, said analog-to-digital converter producing a plurality of sample data;

a constant fraction discriminator responsive to said energy signal;

a time-to-digital converter in communication with said constant fraction discriminator, said time-to-digital converter producing a time value related to a start time of the event; and a processor receiving said time value and said plurality of sample data, wherein said processor determines the total energy level resulting from the event.

2. The apparatus of claim 1 wherein said time-to-digital converter can resolve a time interval which is less than a sampling time interval of said analog-to-digital converter.

3. The apparatus of claim 1 wherein said analog-to-digital converter obtains at least one sample from said shaped signal.

4. The apparatus of claim 1 wherein said processor time-shifts said plurality of sample data based on said time value and produces a plurality of time-shifted data.

5. The apparatus of claim 4 wherein said processor calculates a new amplitude for each of said plurality of time-shifted data.

6. The apparatus of claim 4 wherein said processor matches said plurality of time-shifted data to a reference curve.

7. The apparatus of claim 1 wherein said processor matches said plurality of sample data to a reference curve using said time value.

8. The apparatus of claim 1 wherein said processor includes means for calculating the total energy level from said start time and said plurality of sample data.

9. The apparatus of claim 1 wherein said processor sums the product of each of said plurality of sample data and a sampling time interval of said analog-to-digital converter.

10. An apparatus for determining a total energy level for an event detected in a tomograph scanner, said apparatus comprising:

a detector responsive to the event and producing an energy signal;

a shaping circuit responsive to said energy signal and producing a shaped signal;

an analog-to-digital converter continuously sampling said shaped signal, said analog-to-digital converter producing a plurality of sample data;

a constant fraction discriminator responsive to said energy signal;

a time-to-digital converter in communication with said constant fraction discriminator, said time-to-digital converter producing a time value related to an arrival time of the event, said time-to-digital converter resolving a time interval less than a sampling time interval of said analog-to-digital converter; and a processor receiving said plurality of sample data and said time value, said processor time-shifting said plurality of sample data based on said time value and producing a plurality of time-shifted data, said processor calculating a new amplitude for each of said plurality of time-shifted data, said processor producing an output of the total energy level resulting from the event.

11. An apparatus for determining a total energy level for an event detected in a tomograph scanner, said apparatus comprising:

a means for detecting the event and producing an energy signal;

a means for determining a starting time of the event;

a means for producing a plurality of measured energy levels corresponding to a regular time interval;

a means for correlating said starting time to said plurality of measured energy levels; and a means for determining the total energy level of the event from said starting time and said plurality of measured energy levels.

12. A method for determining a total energy level for an event detected in a tomograph scanner, said method comprising the steps of:

a) detecting the event;

b) determining a start time of the event;

c) producing a shaped energy signal of the event;

d) producing a plurality of measured energy levels from said shaped energy signal, each of said plurality of measured energy levels corresponding to a regular time interval; and e) determining the total energy level from said plurality of measured energy levels and said start time.

13. The method of claim 12 wherein said step of determining the total energy level includes the steps of:

time-shifting said plurality of measured energy levels based on said start time, and calculating a new amplitude for each of said plurality of measured energy levels.

14. The method of claim 12 wherein said step of determining the total energy level includes the step of correlating said plurality of measured energy levels and said start time to a shaped energy curve, wherein said shaped energy curve represents a corrected estimate of the total energy level.

* * * * *